United States Patent
Kruse et al.

(10) Patent No.: US 8,992,978 B2
(45) Date of Patent: Mar. 31, 2015

(54) MATERIAL COMPOSITIONS WHICH COMPRISE ADULT STEM CELLS OBTAINED FROM EXOCRINE GLANDULAR TISSUE, IN PARTICULAR FOR USE IN REGENERATIVE MEDICINE

(71) Applicant: Fraunhofer-Gesellschaft Zur Forderung Der Angewandten Forschung E.V., Munich (DE)

(72) Inventors: Charli Kruse, Herrnburg (DE); Jennifer Kajahn, Bern (CH); Norbert W. Guldner, Lubeck (DE)

(73) Assignee: Fraunhofer-Gesellschaft zur Förderung der Angew Andten Forschung E.V., München (DE)

( * ) Notice: Subject to any disclaimer, the term of this patent is extended or adjusted under 35 U.S.C. 154(b) by 30 days.

(21) Appl. No.: 13/675,133

(22) Filed: Nov. 13, 2012

(65) Prior Publication Data

US 2013/0142860 A1    Jun. 6, 2013

Related U.S. Application Data

(62) Division of application No. 12/670,587, filed as application No. PCT/EP2008/005680 on Jul. 11, 2008, now abandoned.

(30) Foreign Application Priority Data

Jul. 25, 2007    (DE) .................. 10 2007 034 679

(51) Int. Cl.
*A61K 9/14* (2006.01)
*A61K 35/12* (2006.01)
*A61F 2/00* (2006.01)
*A61K 9/48* (2006.01)
*C12N 5/00* (2006.01)
*A61K 9/70* (2006.01)
*A61K 35/55* (2006.01)
*C12N 5/077* (2010.01)
*C12N 5/071* (2010.01)
*A61K 35/34* (2006.01)
*A61K 35/38* (2006.01)
*A61K 35/39* (2006.01)

(52) U.S. Cl.
CPC . *A61K 9/70* (2013.01); *A61K 35/55* (2013.01); *C12N 5/0657* (2013.01); *C12N 5/0676* (2013.01); *A61K 35/34* (2013.01); *A61K 35/38* (2013.01); *A61K 35/39* (2013.01); *C12N 2500/25* (2013.01); *C12N 2501/115* (2013.01); *C12N 2501/135* (2013.01); *C12N 2502/1329* (2013.01); *C12N 2506/22* (2013.01); *C12N 2533/30* (2013.01)
USPC ........... 424/484; 424/423; 424/550; 424/569; 435/377

(58) Field of Classification Search
CPC ....... A61K 35/34; A61K 35/38; A61K 35/39; A61K 35/55; A61K 9/70
See application file for complete search history.

(56) References Cited

U.S. PATENT DOCUMENTS

| | | |
|---|---|---|
| 8,017,389 B2 | 9/2011 | Phillips et al. |
| 2004/0197367 A1 | 10/2004 | Rezania et al. |
| 2005/0014254 A1 | 1/2005 | Kruse |
| 2008/0026611 A1 | 1/2008 | Kanesashi |
| 2009/0220565 A1* | 9/2009 | Guldner et al. ............... 424/423 |

FOREIGN PATENT DOCUMENTS

| | | |
|---|---|---|
| DE | 103 28 280 | 1/2005 |
| DE | 102006003996 | 8/2007 |
| DE | 102007034678 | 3/2008 |
| WO | WO 02/057430 A2 | 7/2002 |
| WO | WO 02/083864 A2 | 10/2002 |
| WO | WO 03/091398 A2 | 11/2003 |
| WO | WO 2004/050133 A2 | 6/2004 |
| WO | WO 2005/001072 A1 | 1/2005 |
| WO | WO 2005/001076 A2 | 1/2005 |
| WO | WO 2005/113747 A2 | 12/2005 |
| WO | WO 2007/085475 A2 | 8/2007 |

OTHER PUBLICATIONS

Kruse et al. Pluripotency of adult stem cells derived from human and rat pancreas Appl. Phys. A 79, 1617-1624 ; 2004.*
Rangappa et al. Cardiomyocyte-mediated contact programs human mesenchymal stem cells to express cardiogenic phenotype.J Thorac Cardiovasc Surg 2003;126:124-32.*
Jihyun Yoon et al., "Transdifferentiation of mesenchymal stem cells into cardiomyocytes by direct cell-to-cell contact with neonatal cardiomyocyte but not adult cardiomyocytes" Annals of Hematology, Springer, Berlin, DE, pp. 715-721.
Jihyun Yoon et al., "Transdifferentiation of mesenchymal stem cells into cardiomyocytes by direct cell-to-cell contact with neonatal cardiomyocyte but not adult cardiomyocytes" Annals of Hematology, Springer, Berlin, DE, vol. 84, pp. 715-721; 2005.
Orlic et al., "Letters to Nature", Macmillan Magazines Ltd, Nature vol. 410, pp. 701-705, Apr. 5, 2001.
Guldner et al., "Autonomously contracting human cardiomyocytes generated from adult pancreatic stem cells and enhanced in co-cultures with myocardial biopsies" International Journal of Artificial Organs, Milan, IT, vol. 29, No. 12, Dec. 1, 2006, pp. 1158-1166.

(Continued)

Primary Examiner — Maria Leavitt
(74) Attorney, Agent, or Firm — Pearl Cohen Zedek Latzer Baratz LLP (57) ABSTRACT

The invention relates to material compositions comprising adult stem cells obtained from exocrine gland tissue and a supporting matrix having the shape of a thread structure and/or of a net. The supporting matrix preferably consists of a plastic material which is physiologically acceptable and degradable in the body. The material compositions of the invention are in particular suited for use in regenerative medicine, e.g. for regeneration of injured or damaged myocard tissue.

3 Claims, 4 Drawing Sheets (56) References Cited

OTHER PUBLICATIONS

Tomita S. et al., "Autologous Transplantation of Bone Marrow Cells Improves Damaged Heart Function" Circulation, Lippincott Williams & Wilkins, US, vol. 110, No. Suppl. 19, Nov. 9, 1999, pp. II-247.

Jihyun Yoon et al., "Transdifferentiation of mesenchymal stem cells into cardiomyocytes by direct cell-to-cell contact with neonatal cardiomyocyte but not adult cardiomyocytes" Annals of Hematology, Springer, Berlin, DE, pp. 715-721, 2005.

Wu et al., "Stem cells: New cell source for myocardial constructs tissue engineering" Medical Hypotheses, Eden Press, Penrith, US, vol. 67, No. 6, Jan. 1, 2006, pp. 1326-1329.

Muller-Borer BJ et al., Am J Pathol. Jul. 2004;165(1):135-45. Adult-derived liver stem cells acquire a cardiomyocyte structural and functional phenotype ex vivo).

Office Action of U.S. Appl. No. 12/670,587, dated Jul. 13, 2012.

Maass, Antje et al., Towards a pragmatic strategy for regenerating infarcted myocardium with glandular stem cells, Annals. of Anatomy, vol. 191, pp. 51-61, 2009.

\* cited by examiner

1: BTS (bidirectionally transformable stem cell patch)
2: Transformation of stem cells to heart muscle cells
3: Transformation and nutrient supply by capillarisation
*: without epicardium
**: with muscle fascia
M: myocardium
LV: left ventricel
MLD: Musculus latissimus dorsi (= broad muscle of back)
o——o: fixation

MATERIAL COMPOSITIONS WHICH COMPRISE ADULT STEM CELLS OBTAINED FROM EXOCRINE GLANDULAR TISSUE, IN PARTICULAR FOR USE IN REGENERATIVE MEDICINE

CROSS-REFERENCE TO RELATED APPLICATIONS

This application is a divisional of U.S. patent application Ser. No. 12/670,587, filed Jun. 29, 2010, now abandoned, which is a National Phase Application of PCT International Application No. PCT/EP2008/005680, International Filing Date Jul. 11, 2008, claiming priority from German Patent Application No. DE 10 2007 034 679.6, filed Jul. 25, 2007, all of which are incorporated by reference herein.

BACKGROUND OF THE INVENTION

Heart failure is one of the main causes of death in industrialised countries and is a result of the inability of mature heart muscle cells (cardiomyocytes) to divide and replace damaged heart muscle. Since the therapeutic use of embryonic cardiomyocytes is prohibited in most countries, adult human stem cells could represent an alternative for regenerative medicine. Adult stem cells of differing origin have previously been injected intramyocardially in order to be converted to cardiomyocytes. However, only in animal experiments has such cell-to-cell contact induced mesenchymal stem cells to differentiate into cardiomyocytes. Therefore, in particular the use of human cardiomyocytes from human adult stem cells for the regeneration of injured or damaged myocardium is a goal that for many years has been striven for but not yet been achieved in an optimal manner.

In DE 10 2006 003 996.3 said object has been principally achieved by providing a method for producing autonomously contractile heart muscle cells by differentiation from adult stem cells that have been isolated from exocrine gland tissue and by providing specific material compositions containing said stem cells.

Said cellular compositions which e.g. comprise injectable cellular compositions, may, in some instances, have the drawback that the cells arrive at the desired application site but do not remain there (e.g. possible in the case of an injection) or that the material composition is rather voluminous which delays the desired resorption in the body and requires more space in the body (e.g. in the case that conventional solid supporting materials are used).

SUMMARY OF THE INVENTION

The present invention is based on the finding that these drawbacks can be avoided by providing new material compositions, wherein the stem cells are present on supporting matrices in the form of preferably resorbable thread structures or nets, on which the stem cells can be induced to differentiate, for example into autonomously contractile heart muscle cells.

The inventors have observed that the adult stem cells isolated from exocrine gland tissue are pluripotent and have both the potential for spontaneous differentiation into heart muscle cells and are capable of developing under suitably stimulating conditions, mainly or almost exclusively, into heart muscle cells. Exocrine gland tissue therefore represents a very effective source for stem cells capable of a wide-ranging differentiation from which the desired heart muscle cells can be successfully obtained in large numbers with good yields.

The exocrine gland tissue used according to the invention may stem from a mature organism, a juvenile organism or a non-human foetal organism, preferably a post-natal organism. The term 'adult' as used in the present application therefore relates to the development stage of the source tissue and not to that of the donor organism from which the tissue originates. 'Adult' stem cells are non-embryonic stem cells.

Preferably, the exocrine gland tissue is isolated from a salivary gland, a tear gland, sebaceous gland, sweat gland, from glands of the genital tract including the prostate gland or from gastro-intestinal tissue, including the pancreas or secretory tissue of the liver. In a particularly preferable embodiment, it is acinar tissue. Especially preferably, the acinar tissue stems from the pancreas, the parotic gland or the mandibular gland.

An advantage of this method resides in that the stem cells can be effectively obtained from living donor organisms, for example from human salivary glands or, by means of a minimally invasive retroperitoneal procedure, from the pancreas without the donor organism being decisively affected. This is particularly advantageous both from ethical standpoints and in view of the possibility of further observation of the donor organism with regard to possible diseases.

According to a first embodiment of this method, the stem cells primarily isolated from the organism are used as a source for further cultivation and differentiation all the way through to heart muscle cells. This version has the advantage of a particularly simple operation. The desired differentiated cells can be obtained directly from a primary culture. Alternatively, according to another embodiment it is provided that, initially, aggregation of the stem cells isolated from the organism to 'organoid bodies' takes place.

This version has the advantage that an effective reservoir for relatively large quantities of differentiated cells is created with the organoid bodies. The inventors have found that the stem cells isolated from the exocrine gland tissue form organoid bodies which, when supplied with nutrients, show strong growth to tissue bodies with diameters of up to a few millimeters or more.

This method can essentially be carried out in such a way that heart muscle cells which have formed spontaneously from the primary or secondary (from the organoid bodies) isolated stem cells are identified, where necessary selected, and further multiplied. According to a preferred embodiment, on the differentiation of heart muscle cells, stimulation of the cell culture is provided. Stimulation has the advantage of increased effectiveness and speed in the formation of the desired heart muscle cells. According to a first version, following the differentiation of the stem cells to heart muscle cells, their stimulated multiplication in a cultivation medium is carried out. According to a second version, the stimulation takes place at an earlier stage and concerns the still undifferentiated stem cells the development/differentiation of which into the desired heart muscle cells is instigated.

Said stimulation may comprise one or more of the following stimulation treatments, which can be carried out simultaneously or consecutively. Co-cultivation with differentiated heart muscle cells or with cell lines derived therefrom, treatment (imprinting) with immobilised or dissolved molecular differentiation factors provided in the liquid phase or genetic activation in the stem cell can be provided. In addition, stimulation can comprise the addition of other substances, such as hormones (e.g. insulin) or cell types which influence the differentiation.

If the imprinting takes place with immobilised growth factors, then differentiation factors fixed to a mobile carrier which can be positioned relative to the stem cells are preferably used. Advantageously, targeted differentiation of individual stem cells or particular stem cell groups can be achieved thereby. The carrier is, for example, a synthetic substrate, which has advantages for targeted design with the differentiation factors, or a biological cell on the cell membrane of which the differentiation factors are arranged.

Some examples of non-limiting growth factors and differentiation factors that can be used are 5'-azacytidine, bFGF, Cardiogenol, transferrin and PDGF.

In a specific embodiment, the stimulation treatment is carried out by cultivation of the stem cells under normal conditions (e.g. as described in example 1) in the presence of biological "nanostructured surfaces". This term herein denotes cells, for example cardiomyocytes or other heart cells, which have been killed by fixation treatment, e.g. with formaldehyde or another suitable fixing agent, and their cell membranes thereby made impermeable, whereas the surface structure of the cells, including the surface proteins and other molecules exposed there, remain intact. By this means, the influence of substances from the interior of these cells is precluded and stimulation takes place specifically through the influence of the surface structure of the fixed cells.

If, according to another preferred embodiment of the method, identification and selection of the differentiated cells from the cell culture are provided, advantages can result for the further use of the heart muscle cells formed. In particular, a cell composition can be provided which consists entirely or largely of heart muscle cells. If the selection takes place with sorting methods which are per se known, such as a preparatory cell sorter method or sorting in a fluid microsystem, advantages can result in terms of compatibility with conventional cell biology procedures.

A further advantage of identification and selection lies therein that cells which are not identified as heart muscle cells and are accordingly not selected from the culture being processed, can be subjected to further cultivation and differentiation. By this means, advantageously, the yield of the method can be increased.

Possibilities for sorting cardiomyocytes and their progenitor cells are, for example, by means of transfection of reporter gene constructs with heart-specific promoters which lead to fluorescing products when they are switched on, or fluorescence-marked antibodies against heart-specific proteins.

According to a preferred embodiment, in order to form the heart muscle cells, stem cells from tissue of secretory glands or glands of the gastro-intestinal tract are obtained from the organism. The stem cells are isolated, in particular, from tissue which consists of acinar tissue or contains acinar tissue. When harvesting from the pancreas takes place, advantages can result in terms of the use of other tissue components of the pancreas for the aforementioned stimulation. If harvesting from the salivary gland is carried out, advantages can arise in terms of the conservative treatment of the donor organism.

Preferred donor organisms are vertebrates and, in particular, mammals. Especially preferred is the human. When human stem cells are used, isolation of the stem cells is performed from non-embryonic states, that is, from differentiated tissue in the juvenile or the adult phase. In the case of non-human donor organisms, use can essentially also be made of differentiated tissue in the foetal condition.

The heart muscle cells produced are preferably used therapeutically. A particular advantage lies therein that human heart muscle cells can be produced from non-embryonic stem cells and used for treatment in humans. A particularly attractive possibility is the autologous treatment of a human with heart muscle cells obtained from stem cells from the human him- or herself. By this means, rejection reactions can be effectively avoided. Typically, the treatment would comprise the regeneration of injured or damaged myocardium. The treatment can either comprise the administration of undifferentiated stem cells and their induced differentiation to heart muscle cells in the body or the administration of already differentiated heart muscle cells, for example, in a transplant.

One subject of the invention are cell compositions which contain adult stem cells from differentiated exocrine gland tissue and/or heart muscle cells derived therefrom. According to a preferred embodiment of the invention, the cell composition may contain other cells or materials which form, for example, a matrix. The cell composition may also comprise a covering or a 3-dimensional matrix in which the heart muscle cells and possibly other cell types are arranged. The covering or 3-dimensional matrix comprises, for example, alginate, collagen, implantable materials, polymers (biopolymers or synthetic polymers), particularly materials that are degradable in the body. The matrix may have a thread-like or net-like structure.

A main aspect of the present invention relates to a material composition wherein the glandular stem cells obtained from exocrine gland tissue are present on a supporting matrix which has the shape of threads or nets. This supporting matrix is preferably physiologically tolerable and degradable in the body. Typically, it is a plastic material capable to be resorbed, e.g. the commercially available Vicryl (from Ethicon) or the above mentioned polymeric materials. The glandular stem cells adhere on the external surface as well as in the microstructures of the threads and nets and can be induced to differentiate there. By use of this supporting matrix the stem cells and the differentiated cells derived therefrom, respectively, can be transferred to desired application sites in the body conveniently and in a targeted manner. Moreover, the application of such a supporting matrix might be able to prevent the arrhythmic disorders often observed in the context of intramyocardial injection of stem cells. By using such a supporting matrix also cell loss (e.g. by migration of stem cells after injection) can be delayed or prevented, since the applied cells adhere tightly to the microstructures of the threads and nets and regenerate the damaged tissue only by means of or upon division.

A specific embodiment of the present invention concerns a bidirectionally transformable stem cell patch (BTS) for myocardial regeneration. A patch of this type comprises adult stem cells from exocrine gland tissue, preferably pancreatic stem cells, and a porous, possibly subdivided, matrix for accommodating the cells, has a large supporting surface for the myocardial wound surface onto which it should be applied after removal of the epicardium, is usually multi-layered, for example, constructed from a plurality of sponge-like membranes, but relatively thin (having a short diffusion path) and readily fixable.

The porous matrix is, for example, a collagen matrix or consists of another physiologically tolerable material (e.g. as described above). The supporting matrix may be present in the shape of a thread structure or a net as defined above. In one embodiment, all the materials of the patch are degradable in the body.

The patch can also contain cells which have fully or partially differentiated out to heart muscle cells or other differentiated cells present in the heart. The patch can also contain substances which promote the differentiation of stem cells to cardiomyocytes and/or pharmaceutically active agents, for example for suppressing a rejection reaction.

The term "bidirectionally transformable" as used herein, indicates that the patch is configured such that the cells contained within said patch, in particular stem cells, can get into contact on both sides with cells from the adjacent tissue or with substances produced by the cells and a transformation/differentiation of the stem cells into the desired cell type can thereby be induced or stimulated.

Figure 3:
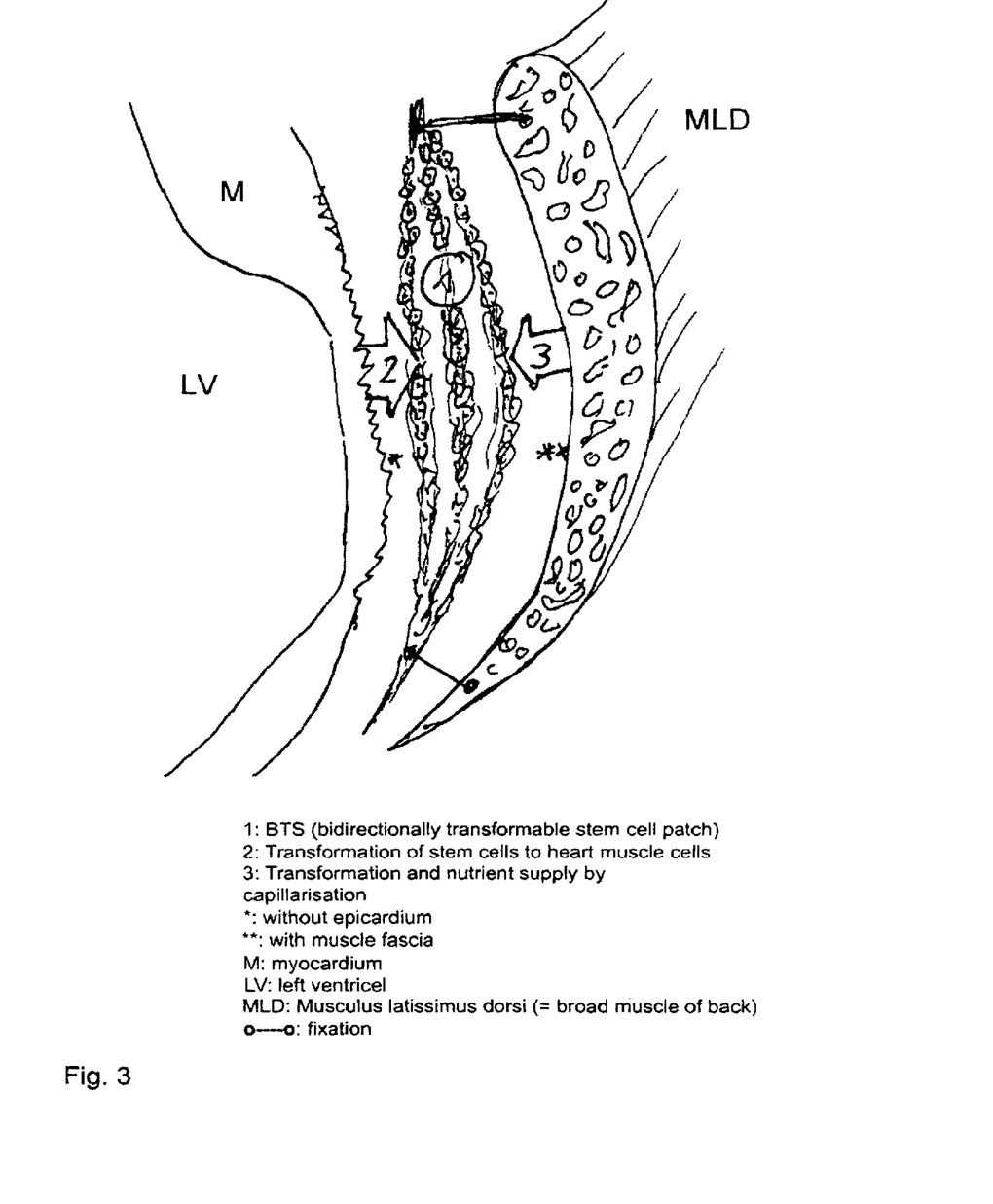
FIG. 3 shows the placement of a bidirectionally transformable stem cell patch (BTS) between the myocardium and the broad back muscle (*Musculus latissimus dorsi*) for myocardial regeneration.
Figure 4:
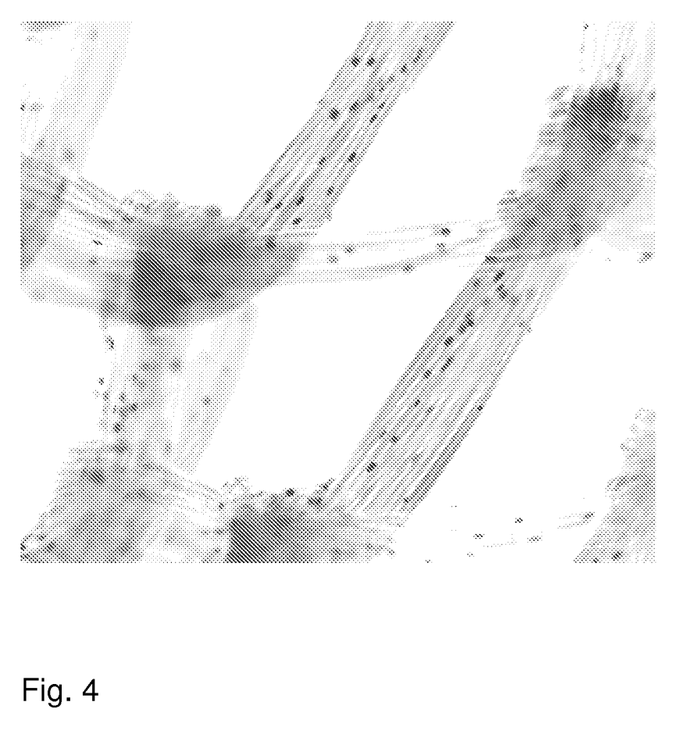
FIG. 4 shows thread-like structures with glandular stem cells grown thereupon.

In a preferred embodiment, the patch is placed between the broad back muscle (*Musculus latissimus dorsi*) and the myocardium freed from epicardium (see FIG. 3). The cells of the myocardium or substances produced thereby can then induce differentiation of the stem cells arranged in the patch on the side towards the heart into heart cells, in particular, heart muscle cells. On the other side, the tissue of the back muscle can, on the one hand, provide the cells of the patch with nutrients and, on the other hand, induce transformation of the stem cells on the side towards the back to vessel cells, for example, endothelial cells etc., or permit migration of appropriate cells into the patch, so that formation of new capillary vessels can take place in the patch or the adjoining tissue. If desired, hypercapillarisation of the back muscle covering with intact muscle fascia is induced in the patient by intermittent transcutaneous electrostimulation (e.g. with stimulation electrodes stuck on).

In another preferred embodiment, the stem cells are injected into the (preferably hypercapillarised) muscle tissue (*M. latissimus dorsi*) itself, which wraps round the heart. There they develop and become transformed into heart muscle cells by substances from the adjoining injured myocardial surface (and/or by exogenous differentiation factors that are fed in). The vascular system of the skeletal muscle then becomes the vascular system of the contractile myocardial patch. By means of an implanted muscle pacemaker which electrostimulates the patch, transformation of the muscle fibres of the skeletal muscle into pure, oxygen-dependent type I fibres could be induced. Since, in contrast to the heart muscle fibres, type I fibres cannot survive continuous stimulation, this would in the long term lead to elimination of these skeletal muscle fibres. A myocardial patch with its own vascular supply would be the result.

According to a particularly preferred embodiment of the invention, the adult stem cells used are human stem cells that have been isolated from pancreatic tissue.

Adult stem cells were isolated and cultivated from pancreatic tissue of patients who had undergone a pancreas operation (see example 1 with regard to the conditions). The cells were selected, cultivated with medium (e.g. DMEM) with foetal calf serum and passaged up to more than 25 times. The cultures could also be frozen between individual passages without impairing the cells. In different passages, the cultures showed spontaneously formed reticular cell clusters (FIG. 1a) and some of these cell clusters showed cellular contractions at various sites, indicating a functional contractile system. In an optimized method with which relatively large quantities of contractile heart muscle cells (cardiomyocytes) could be obtained faster, pancreatic stem cells were co-cultivated with small pieces of human heart muscle obtained from a cardiac valve operation. Following a contact time of 48 hours, the myocardium was removed and stem cells were held in culture for a further 2 to 4 days or 2 weeks in order to investigate the influence of the myocardium on differentiation to cardiomyocytes. Thereafter, the various methods, including immunocytochemistry of sarcomeres and heart-specific troponin I, semiquantitative RT-PCR analysis with regard to alpha-actin and troponin T2, and electron micrographic examination, were applied in order to identify cardiomyocytes.

Myocardium for co-cultivation can be obtained by means of biopsies from the cardiac septum, which are already routinely used for the detection of tissue rejection following heart transplantation. The method according to the invention, with which a large number of contractile cardiomyocytes can be produced by easy and convenient means, could be significant for general myocardial regeneration and, in particular, for contractile myocardial patches.

BRIEF DESCRIPTION OF THE DRAWINGS

FIG. 1a Cultures of pancreatic stem cells with reticular cell clusters show autonomous contractions.

FIG. 1b Immunocytochemical visualisation of sarcomeres (red) in transformed adult pancreatic stem cells (blue nuclei) in contact with human myocardium (M) for 2 days. A falling gradient of M towards the periphery is observable.

FIG. 1c A gene expression analysis with heart-specific PCR primers for the target genes α-actin and troponin T2 isoform-demonstrates a strong increase in muscle cell-specific molecules in co-cultivated cells (CEpan 3b, human pancreatic stem cells; P14, passage 14; HEp-2, human carcinoma cell line; h-heart-cDNA, human heart-cDNA).

FIG. 2a,b Human pancreatic adult stem cells with immunocytochemical staining for heart-specific troponin I without contact with human myocardium (a) and following a two-day contact with human myocardium (b). Clear evidence of the presence of heart-specific troponin I in transformed cells is given.

FIG. 2c,d Various stages of cardiomyocytes, transformed from adult pancreatic stem cells, are shown in the electron micrographs taken four days after 48-hour contact with biopsies of human myocardium. Myofilaments and structures of partial (c) and complete (d) development of the intercalated disks are shown. Vesicles, organised in lines (FIG. 2c, arrows), are considered as cross-sections of a premature status of the sarcoplasmic reticulum.

DETAILED DESCRIPTION OF THE INVENTION

Example 1

Isolation, Cultivation and Co-Cultivation of Adult Pancreatic Human Stem Cells

The source of the human pancreatic tissue was healthy tissue that had been removed for precautionary reasons during a pancreas operation due to cancer or inflammatory disease. The tissue was obtained in physiological saline solution. Pancreas acini were isolated therefrom, as previously described (DE 10328280; Orlic et al., Nature 410: 701-705).

In particular, the pancreatic tissue was treated with a digestant containing HEPES-Eagle's Medium (pH 7.4), 0.1 mM HEPES buffer (pH 7.6), 70% (vol/vol) modified Eagle's Medium, 0.5% (vol/vol) Trasylol (Bayer AG, Leverkusen, Germany), 1% (wt/vol) bovine serum albumin, 2.4 mM $CaCl_2$ and collagenase (0.63 PZ/mg, Serva, Heidelberg, Germany). Following digestion, the acini were dissociated by suction and ejection using different glass pipettes with narrow openings, and filtered through a nylon sieve. The acini were centrifuged and further cleaned by washing in Dulbecco's modified Eagle's Medium (DMEM, Gibco, Germany), with added 20% foetal calf serum (FCS), equilibrated with Carbogen and brought to pH 7.4. The washing procedure (centrifuging, suction, resuspension) was repeated 5 times. The acini were resuspended in DMEM and cultivated at 37° C. in a humid atmosphere with 5% $CO_2$. After 1-2 days of culturing, spindle-shaped cells were observed, surrounding the outer edges of the pancreatic acini. Differentiated acinar cells were removed in each medium exchange. After reaching confluency, pancreatic stem cells were cultivated by means of trypsin treatment, cultivated, counted and resown at a density of $2.4 \times 10^5$ cells/$cm^2$. This procedure was repeated until sufficient cells were available. As previously shown, no changes occur in the stem cells during the passages (tested by staining). We therefore used passages 14 and 4 for further differentiation.

Stimulation of differentiation into cardiomyocytes was achieved by co-cultivation of the primary cells with 5 pieces of myocardium (4×4×4 mm) in each case for 2 days. The tissue (mitral papillary muscle or auricle) was obtained during an operation for heart valve replacement and transported in physiological saline solution. The heart muscle pieces were placed on the bottom of the culture vessels for 3 hours until the primary cells ($1 \times 10^6$) were applied. After 48 hours, the heart muscle pieces were removed and the stem cells further cultivated as described above. The cells were then subjected to a passage each time after reaching confluency. Immunocytochemical analyses were carried out directly 48 hours after treatment. In order to investigate the long-term effects of differentiation, the cells were harvested 17 days after treatment for PCR analyses.

Figure 1:
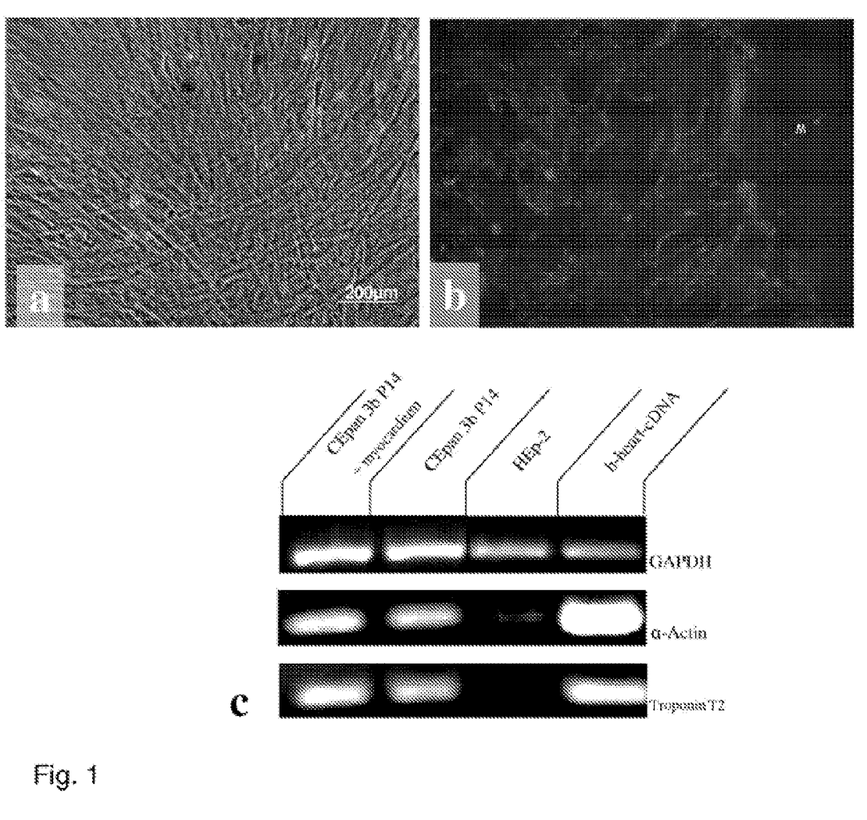
FIGS. 1 and 2 show the results of various identification methods for cardiomyocytes.

As the cells became confluent in the culture dishes, reticular clusters could be observed (FIG. 1a). The cell layer was washed with the less nutrient-rich phosphate buffered salt solution (PBS) and partially lifted mechanically from the base of the culture with a scraper. Contractile regions were then documented with a video system. In order to check whether cardiomyocytes grow from biopsies of cardiac tissue, the biopsies were cultivated as described above, but without pancreatic stem cells. After 2 days, no growing cells could be found.

Example 2

Identification of Heart Muscle Cells

1. Immunocytochemistry of Sarcomeres

Both the stimulated and non-stimulated stem cells were sown on chamber slides and cultivated for at least 2 days before being fixed with methanol:acetone (7:3) containing 1 g/ml DAPI (Roche, Switzerland) and washed 3 times in PBS. Following incubation in 10% normal goat serum at room temperature for 15 minutes, the samples were incubated with the primary antibody overnight at 4° C. in a humidity chamber. Primary monoclonal antibody was directed against sarcomere Myosin MF 20 (DSHB, USA). Following rinsing three times with PBS, the slides were incubated for 45 minutes at 37° C. with Cy3-marked anti-mouse IgG, diluted 1:200. The slides were washed 3 times in PBS and covered with Vectashield mounting medium (Vector, USA) and analysed with a fluorescence microscope (Axioskop Zeiss, Germany). In order to rule out identified sarcomeres being released from the biopsy and adhering to the stem cells, controls with myofibroblasts and endothelial cells were co-cultivated with myocardium. In these controls, the tested cells produced negative results in immunochemistry for sarcomeres.

By contrast, an immunocytochemical identification of sarcomeres was successfully carried out using transformed adult human pancreatic stem cells in four preparations following contact with human myocardium (M) from four different patients. A declining gradient of developed sarcomeres from "M" (placement of the myocardium) up to the periphery was found after two days of myocardial contact (FIG. 1b).

2. Immunocytochemistry of Heart-Specific Troponin I

Stem cells were co-cultivated with myocardial biopsies for 48 hours and cultured for 2 to 4 days after removal of the myocardium. The samples were then rinsed twice with PBS and dried for 24 hours in air at room temperature, and thereafter fixed with pure acetone for 10 minutes at −20° C., rinsed again for 2×5 minutes with TBS buffer and pre-incubated with RPMI 1640 with 10% AB serum. Monoclonal antitroponin I-antibodies (Cone 2d5, Biozal 1:25) were included as primary antibodies for 60 minutes. Addition of secondary antibody (antimouse-rabbit antibody; DAKO; 1:25, for 30 minutes) followed by incubation with a complex with alkaline phosphatase or without alkaline phosphatase (DAKO; 1:50, 30 minutes) was repeated several times. Finally, substrate incubation (naphthol/neofuchsin) and contrast staining with haemalaun was carried out before microscopic examination. In addition, isotope testing was carried out with mouse-IgG 1 (DAKO) and, for a further negative control, skeletal muscle was stained. Myocardium was used as a positive control. An isotype control with mouse-IgG 1 (DAKO) was also negative. Additional controls carried out with skeletal muscle were also negative. As expected, a control with human myocardium showed a positive result (data not shown).

Figure 2:
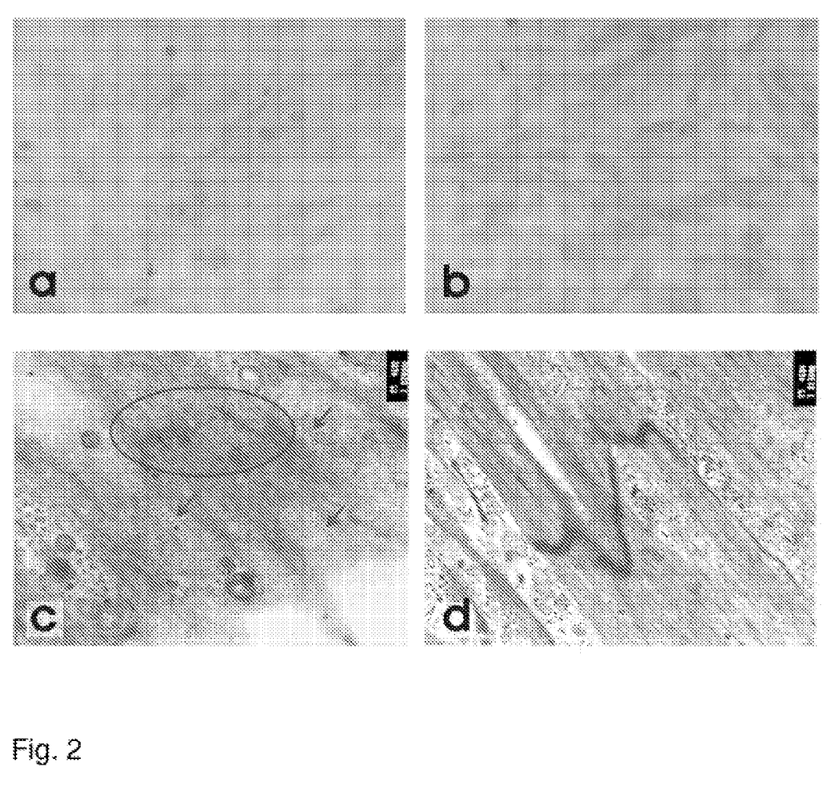

The immunocytochemistry of heart-specific troponin I was already strongly positive 2 days after a 48-hour co-culture with a human myocardial biopsy, as FIG. 2b shows. Stem cells which were not in contact with myocardial biopsies produced mainly negative results in an immunocytochemical test for troponin I and served as a further control (FIG. 2a).

3. Semiquantitative RT-PCR Analysis

Whole-cell RNA was isolated using a Nucleo-Spin® RNA II kit (Macherey-Nagel, Duren, Germany). 0.5 μg total RNA were transcribed in reverse into cDNA using reverse transcriptase Superscript II RNase H⁻ (RT, Invitrogen) and oligo dT primers (Invitrogen) in accordance with the instructions of the manufacturer. The PCR reactions were carried out in a 50 μl reaction volume using Taq DNA polymerase (MBI Fermentas). The reactions were carried out for 38 cycles. A control run of RNA without reverse transcription took place in order to check for contamination with genomic DNA and produced no bands. To normalise the cDNA concentration in different RT samples, we measured the relative expression of GAPDH as a representative control for an internal housekeeping gene. The expected fragment sizes and the optimum PCR annealing temperatures were as follows: GAPDH, 5':gagtcaacggatttggtcgt, 3':ggaagatggtgatgggattt (213 bp, 58.8° C.), troponin T2, 5':gattctggctgagaggagga, 3':tggagactttctggttatcgttg (197 bp, 62.6° C.), alpha-actin, 5':gtgtgacgacgaggagacca, 3':cttctgacccataccacca (154 bp, 62.6° C.). Purified human heart RNA (Ambion) and a carcinoma cell line (HEp2) served as functional controls for the PCR primer.

A semi-quantitative RT-PCR analysis (FIG. 1c) for α-actin and troponin T2 showed a more markedly raised level of these muscle cell-specific molecules two weeks after contact than in untreated spontaneously differentiated stem cells. The increase in α-actin and troponin T2 after two weeks was reproducible and significant.

4. Electron Microscopic Investigation

Cells which had been cultured on cover glasses were fixed for 1 hr with 2.5% glutaraldehyde in 0.1 M cacodylate buffer. Subsequent fixation with 1% $OsO_4$ in 0.1 M cacodylate buffer was carried out for 2 hrs; samples were dehydrated with ethanol and embedded in Araldite (Fluka, Buchs, Switzerland). Ultrathin sections were stained with uranyl acetate and lead citrate (Ultrostainer Carlsberg System, LKB, Bromma, Sweden) and examined with a Philips EM 400 electron microscope (Philips, Eindhoven, Netherlands) at 60 kV.

The electron microscope examination (FIG. 2c,d) shows, after 48 hours of contact of adult pancreatic stem cells with human myocardium and a further 4 days of differentiation, cells with a number of contractile fibrils. Various stages of intercalated disks were also observed. Whereas the intercalated disks in FIG. 2c are only weakly, though clearly, recognisable, in FIG. 2d, the intercalated disk is well differentiated, as in mature tissue. Since intercalated disks are only found in cardiac muscle, these findings also provide evidence of differentiation of adult human stem cells into cardiomyocytes.

After 14-40 days of growth in culture and after 48 hours in contact with human myocardium, the cells were partially mechanically lifted from the culture vessel and treated with a less nutrient-rich culture medium. The cell complexes showed contractions in various regions. These contractions were autonomous and reproducible in several cultures, thereby demonstrating a functional contractile system. This is a first observation of human autonomously contracting myocardium cells produced from human adult stem cells.

Example 3

Differentiation with 5-azacytidine

The stem cells are sown at a density of $1 \times 10^3$ in Petri dishes and cultivated for 24 hours in DMEM (with 10% FKS and 1% penicillin/streptomycin) until they attach adhesively to the base of the culture dishes. The cells are then cultivated for 24 hours in a differentiating medium, containing:
   DMEM medium
   10 µg/l bFGF
   10 µmol/l 5-azacytidine
   0.25 mg/l amphotericin.

A comparison with control batches without 5-azacytidine shows that, on stimulation with 5-azacytidine, significantly more stem cells differentiate to cardiomyocytes.

Example 4

Differentiation with Cardiogenol

The cells are sown in Petri dishes at a density of $1 \times 10^3$ and directly cultivated for 48 hours with a differentiating medium, containing:
   DMEM medium
   500 µl Cardiogenol solution.

For the Cardiogenol solution, 5 mg Cardiogenol are dissolved in 4.75 ml DMSO.

Also in this case, more cardiomyocytes develop than in controls without Cardiogenol.

Example 5

Differentiation with Insulin, Transferrin and PDGF

The cells were incubated for 7 days in the following differentiating medium:
   DMEM medium
   820 µg/ml BSA
   5 µg/ml transferrin
   5 µg/ml insulin
   50 ng/ml PDGF In this case, also, more cardiomyocytes developed than in the controls without growth factors.

Example 6

Differentiation in the Presence of Co-Cultivated Cardiomyocytes

Version 1:
Cardiomyocytes are sown in a culture bottle such that they completely grow over the base of the bottle. Then stem cells (for example, marked with β-galactosidase) were added to the cells at a density of $1 \times 10^3$ and co-cultivated for 14 days. From the marked stem cells, the number of cells differentiated into cardiomyocytes can be determined, for example, with FACS analysis.

Version 2:
Cardiomyocytes are added to freshly sown pancreatic stem cells in a cell culture cage for 14 days. The cardiomyocytes will release various substances which promote the differentiation of the stem cells to cardiomyocytes. Fusion with co-cultivated cells can be ruled out, and the cells do not have to be labelled beforehand.

Example 7

Growth of Glandular Stem Cells on Threads and Nets

Stem cells from exocrine glands of human and goat are sown in different passages onto resorbable threads and nets. These threads and nets for example consist of Vicryl (sterile packed from Ethicon) and are coated with 1% gelatine beforehand. Subsequently, the seeding of the stem cells in DMEM supplemented with 10% FCS is effected. After a few hours already, the stem cells adhere on and in the microstructures of the threads and nets and can then be visualized by the use of different stains, e.g. nucleic stains.

---

The invention claimed is:

1. A bidirectionally transformable stem cell patch, said stem cell patch comprising:
   a) a porous biocompatible matrix having a thread or net structure and adult stem cells isolated from an exocrine gland tissue selected from the group consisting of pancreas, a sweat gland and a salivary gland of a donor organism, said thread or net structure configured for receiving the adult stem cells; and
   b) a supporting surface configured for placing said patch on a myocardial wound surface;

wherein when said patch is placed between the myocardium freed from epicardium and the Latissimus Dorsi Muscle, said adult glandular stem cells contained within said patch contact on both sides with myocardium and Latissimus Dorsi Muscle tissue, wherein contact of cardiomyocytes or substances produced thereby induce differentiation of at least some of the adult glandular stem cells arranged in the patch on the side towards the myocardium wound surface into cardiomyocytes.

2. The stem cell patch according to claim 1, wherein the stem cells are human stem cells.

3. The stem cell patch according to claim 1, wherein the porous matrix is degradable in the body.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Homo sapiens

<400> SEQUENCE: 1
gagtcaacgg atttggtcgt                                        20

<210> SEQ ID NO 2

```
<211> LENGTH: 20
<212> TYPE: DNA
<213> ORGANISM: Homo sapiens

<400> SEQUENCE: 2
ggaagatggt gatgggattt                                              20

<210> SEQ ID NO 3
<211> LENGTH: 20
<212> TYPE: DNA
<213> ORGANISM: Homo sapiens

<400> SEQUENCE: 3
gattctggct gagaggagga                                              20

<210> SEQ ID NO 4
<211> LENGTH: 23
<212> TYPE: DNA
<213> ORGANISM: Homo sapiens

<400> SEQUENCE: 4
tggagacttt ctggttatcg ttg                                          23

<210> SEQ ID NO 5
<211> LENGTH: 20
<212> TYPE: DNA
<213> ORGANISM: Homo sapiens

<400> SEQUENCE: 5
gtgtgacgac gaggagacca                                              20

<210> SEQ ID NO 6
<211> LENGTH: 20
<212> TYPE: DNA
<213> ORGANISM: Homo sapiens

<400> SEQUENCE: 6
cttctgaccc atacccacca                                              20
```